United States Patent
Poulsen

(10) Patent No.: US 9,439,718 B2
(45) Date of Patent: Sep. 13, 2016

(54) RECIPROCATING COOLING MEMBER FOR AN ENERGIZED SURGICAL INSTRUMENT

(71) Applicant: Peter D. Poulsen, Grants Pass, OR (US)

(72) Inventor: Peter D. Poulsen, Grants Pass, OR (US)

( * ) Notice: Subject to any disclaimer, the term of this patent is extended or adjusted under 35 U.S.C. 154(b) by 271 days.

(21) Appl. No.: 14/256,771

(22) Filed: Apr. 18, 2014

(65) Prior Publication Data
US 2015/0297287 A1    Oct. 22, 2015

(51) Int. Cl.
*A61B 18/12*    (2006.01)
*A61B 18/14*    (2006.01)
*A61B 17/32*    (2006.01)
*A61B 18/00*    (2006.01)

(52) U.S. Cl.
CPC ... *A61B 18/1445* (2013.01); *A61B 17/320092* (2013.01); *A61B 2017/320072* (2013.01); *A61B 2018/00005* (2013.01); *A61B 2018/00047* (2013.01); *A61B 2018/00095* (2013.01); *A61B 2018/00101* (2013.01)

(58) Field of Classification Search
CPC ................. A61B 17/320092; A61B 18/1445; A61B 2017/320072; A61B 2018/00005; A61B 2018/00047; A61B 2018/00095; A61B 2018/00101
See application file for complete search history.

(56) References Cited

U.S. PATENT DOCUMENTS

| | | | | |
|---|---|---|---|---|
| 5,443,463 | A * | 8/1995 | Stern | A61N 1/40 606/51 |
| 7,717,915 | B2 | 5/2010 | Miyazawa | |
| 7,909,824 | B2 | 3/2011 | Masuda et al. | |
| 8,147,488 | B2 | 4/2012 | Masuda | |
| 2005/0113819 | A1* | 5/2005 | Wham | A61B 18/1206 606/34 |
| 2005/0203505 | A1* | 9/2005 | Megerman | A61B 18/02 606/41 |
| 2006/0079868 | A1* | 4/2006 | Makin | A61N 7/02 606/27 |
| 2010/0049178 | A1* | 2/2010 | Deem | A61B 18/02 606/9 |
| 2011/0306967 | A1* | 12/2011 | Payne | A61B 18/1445 606/41 |

* cited by examiner

*Primary Examiner* — Daniel Fowler
(74) *Attorney, Agent, or Firm* — David S. Alavi

(57) ABSTRACT

A surgical instrument comprises: an elongated sheath, an energy probe, an elongated energy conductor, and an elongated cooling member. The energy probe is connected to the distal end portion of the sheath. The elongated energy conductor is contained within the sheath and arranged to transmit distally to the energy probe energy from an energy source. The elongated cooling member is reciprocally movable within the sheath and thermally coupled at its proximal portion to a cooler. The cooling member is movable between a proximal, non-cooling position and a distal, cooling position. In the non-cooling position, a distal end of the cooling member is displaced proximally from the energy probe so as to impede thermal conduction therebetween; in the cooling position, the distal end of the cooling member thermally contacts the energy probe so as to facilitate thermal conduction therebetween.

15 Claims, 3 Drawing Sheets

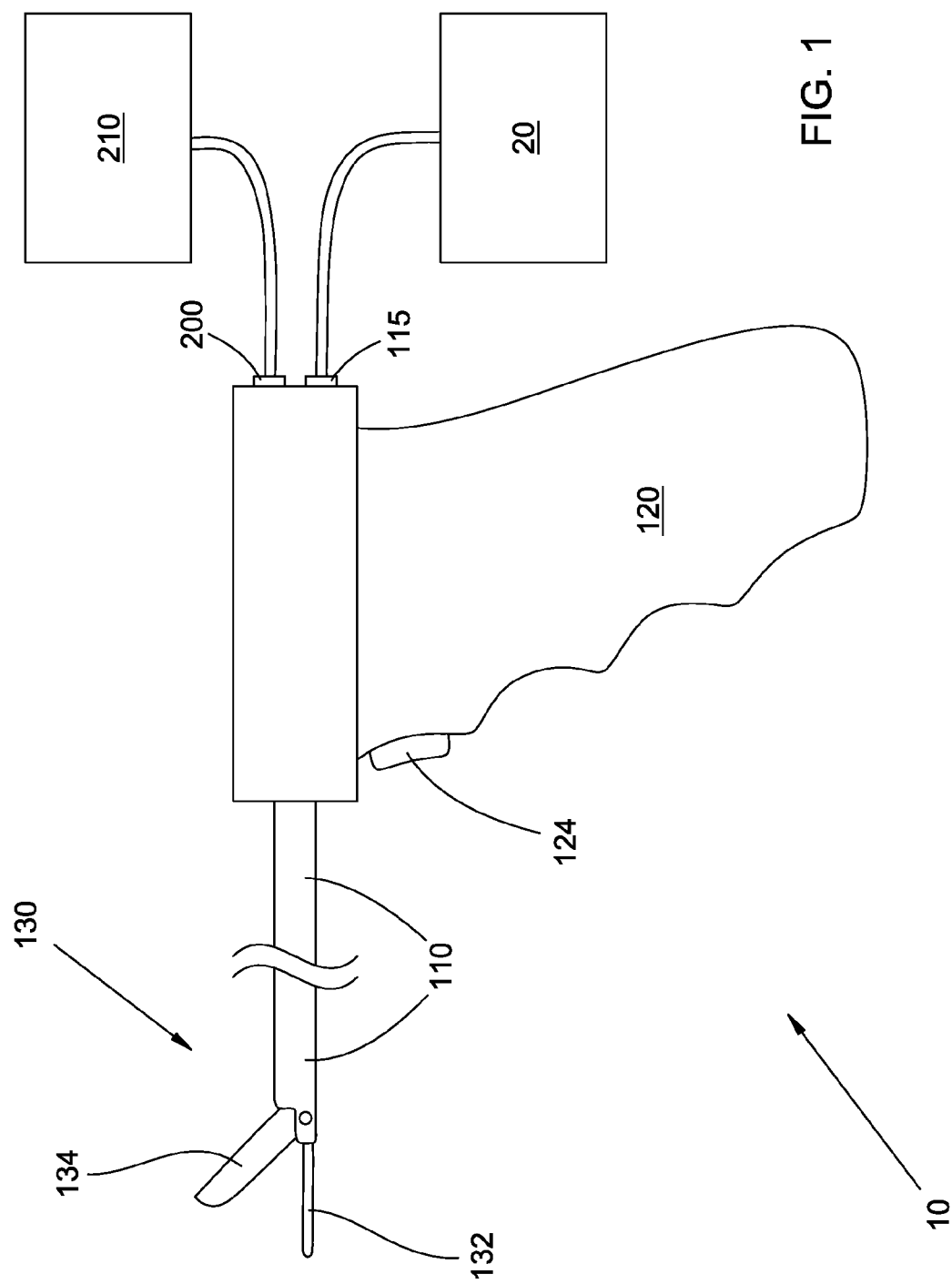

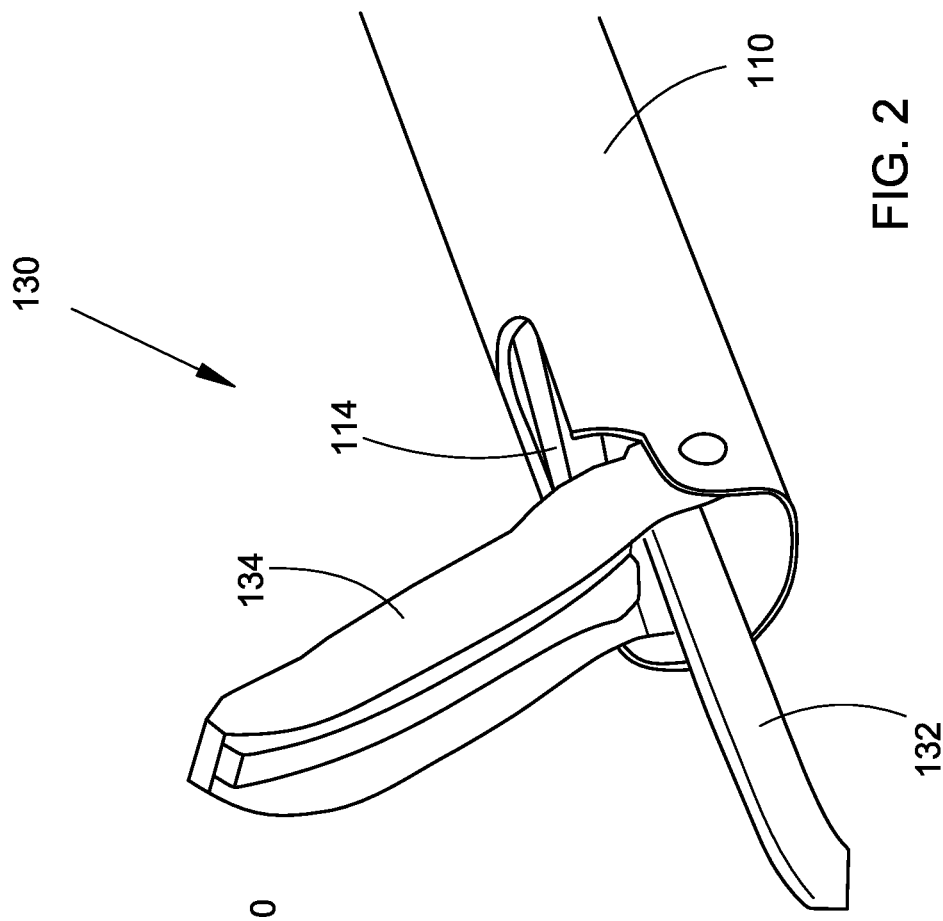
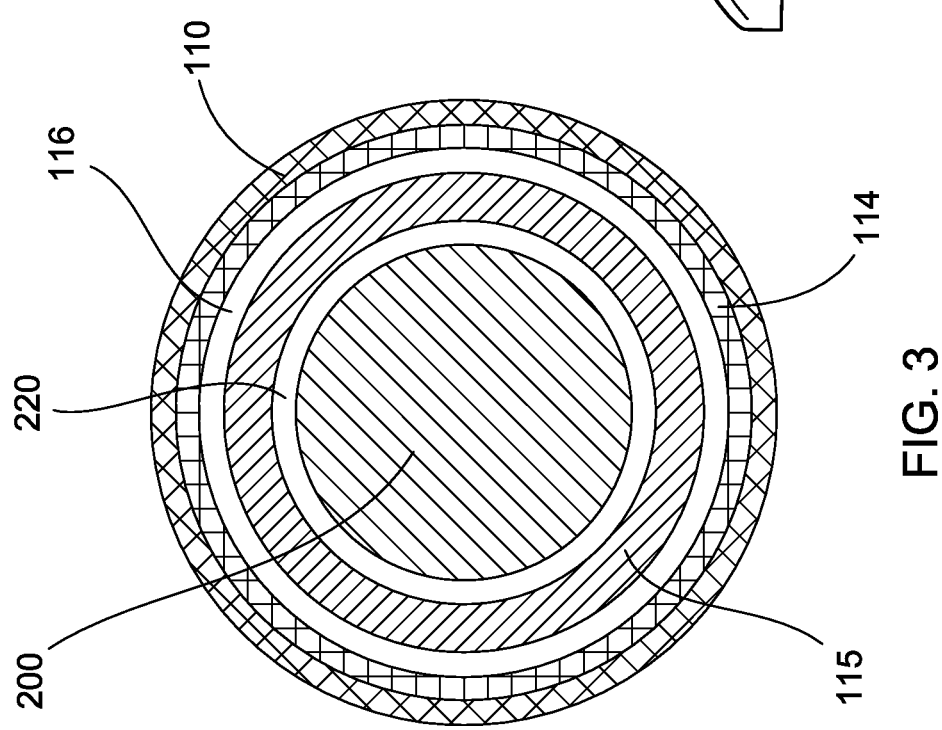

RECIPROCATING COOLING MEMBER FOR AN ENERGIZED SURGICAL INSTRUMENT

BACKGROUND

The field of the present invention relates to surgical instruments. In particular, apparatus and methods are described herein for providing cooling of an energized surgical instrument.

A wide variety of energized surgical instruments (i.e., apparatus) are available. Some of these are described in:

U.S. Pat. No. 7,717,915 entitled "Ultrasonic coagulation and cutting apparatus" issued May 18, 2010 to Miyazawa and assigned to Olympus Medical Systems;

U.S. Pat. No. 7,909,824 entitled "Energy accessory" issued Mar. 22, 2011 to Masuda et al and assigned to Olympus Medical Systems; and U.S. Pat. No. 8,147,488 entitled "Surgical operating apparatus" issued Apr. 3, 2012 to Masuda and assigned to Olympus Medical Systems.

Generally, such an energized surgical instrument is held and actuated by a surgeon using a proximal handle portion; the surgical instrument engages tissue of the surgical patient at a distal portion that can include a probe, jaws, or other structural or functional members. One or more such members can be connected to a source of energy, e.g., ultrasonic, electrical, or other. The energy is transmitted distally along an energy conductor of the instrument to the distal portion to cut, seal, or coagulate selected tissues in the patient's body, typically by heating the tissue. The heat can be conducted from the distal portion of the surgical instrument into the tissue or, more typically, can be generated in the tissue by electrical or ultrasonic energy directed into the tissue by the distal portion of the surgical instrument. An elongated tube or sheath connects the proximal handle and the distal portion and can contain the energy conductor and optionally other members or components, e.g., for mechanically actuating the distal portion.

SUMMARY

A surgical instrument comprises: an elongated sheath, an energy probe, an elongated energy conductor, and an elongated cooling member. The energy probe is connected to the distal end portion of the sheath. The elongated energy conductor is contained within the sheath and arranged to transmit distally to the energy probe energy from an energy source. The elongated cooling member is reciprocally movable within the sheath and thermally coupled at a proximal portion of the cooling member to a cooler. The cooling member is movable between a proximal, non-cooling position and a distal, cooling position. In the non-cooling position, a distal end of the cooling member is displaced proximally from the energy probe so as to impede thermal conduction between the energy probe and the cooling member. In the cooling position, the distal end of the cooling member thermally contacts the energy probe so as to facilitate thermal conduction between the energy probe and the cooling member.

Objects and advantages pertaining to energized surgical instruments may become apparent upon referring to the example embodiments illustrated in the drawings and disclosed in the following written description or appended claims.

This summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

BRIEF DESCRIPTION OF THE DRAWINGS

FIG. 1 is a schematic side elevation view of a cooled, energized surgical instrument.

FIG. 2 is a schematic perspective view of a distal portion of the surgical instrument.

FIG. 3 is a transverse section of a portion of the surgical instrument.

Figure 4:
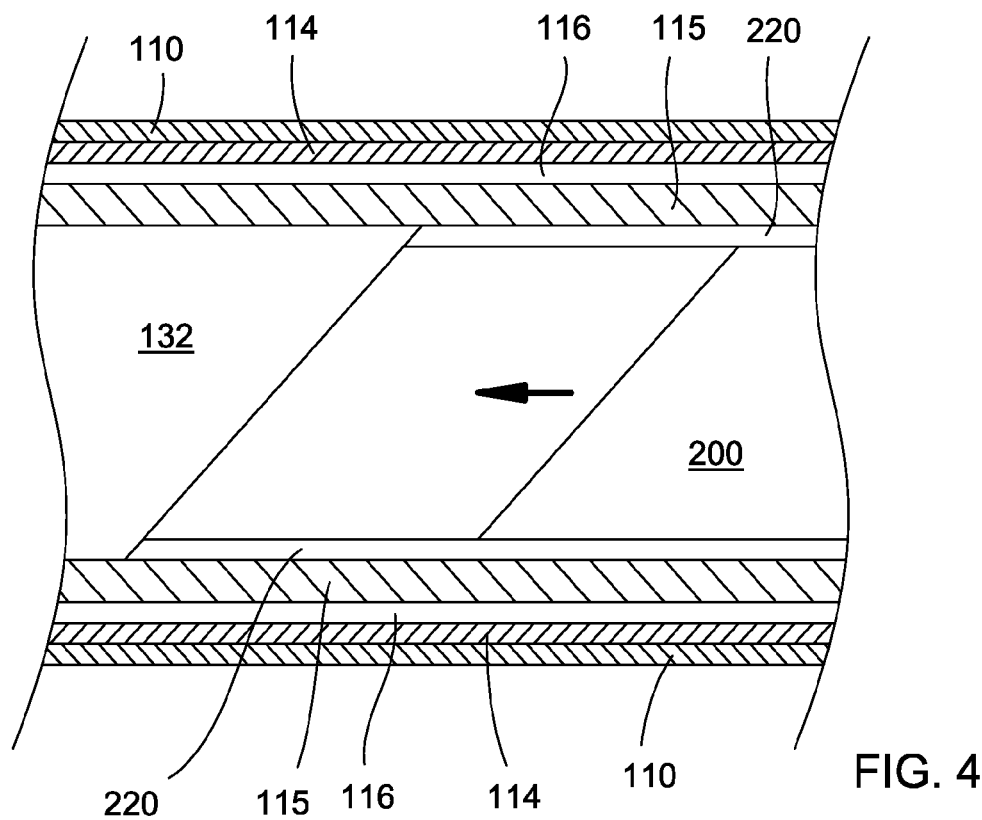
FIG. 4 is a longitudinal section of a portion of the surgical instrument with the cooling member in a proximal, non-cooling position.

It should be noted that the embodiments depicted are shown only schematically, and that not all features may be shown in full detail or in proper proportion. Certain features or structures may be exaggerated relative to others for clarity. In the sectional views of FIGS. 3-5, hatching of thermal or electrical insulators is omitted so as not to clutter the drawing; in the sectional views of FIGS. 4 and 5, hatching of the energy probe and the cooling member is similarly omitted. It should be further noted that the embodiments shown are examples only, and should not be construed as limiting the scope of the present disclosure or appended claims.

DETAILED DESCRIPTION OF EMBODIMENTS

As noted above, tissues of the patient's body can be cut, sealed, or coagulated by heat generated by energizing a surgical apparatus (by conduction of heat from the apparatus or by generation of heat in the tissue by energy delivered in other forms by the surgical apparatus). The amount of heating (temperature and duration) determines the resulting effects on a given tissue type; those effects can continue to accrue even after energy transmission is discontinued, due to residual heat in the tissue or in the distal portion of the surgical instrument. Therefore, it would be desirable to provide, in addition to conventional control of energy transmission to the distal portion of the surgical apparatus, controllable cooling of at least a portion of the distal portion of the surgical apparatus. That cooling capability enables the surgeon to first apply a controlled amount of energy during a selected time interval to heat the targeted tissue, and then to rapidly cool that tissue at the end of the selected time interval. In many instances the distal portion of the energized surgical instrument is employed for tissue dissection or manipulation, in addition to its cutting sealing, or coagulating functions. Cooling of the distal portion of the instrument enables the surgeon to avoid unintended thermal damage to tissues during such dissection or manipulation.

To achieve that goal, the surgical apparatus 10 comprises: an elongated sheath 110 with an energy probe 132 connected to a distal end portion 130 of the sheath 110 (FIGS. 1 and 2). The surgical apparatus can include a handle portion 120 connected to a proximal end portion of the sheath 110. Contained within the sheath 110 are an elongated energy conductor 115 and an elongated cooling member 200 (FIG. 3). The energy conductor 115 is arranged to transmit distally to the energy probe 132 energy from an energy source 20; the energy source 20 and its connection to the energy conductor 115 are shown only schematically in the figures.

The cooling member 200 is reciprocally movable within the sheath 110 and thermally coupled at a proximal portion of the cooling member 200 to a cooler 210; cooler 210 and its connection to the cooling member 200 are shown only schematically in the figures. The cooling member 200 is movable between a proximal, non-cooling position (FIG. 4) and a distal, cooling position (FIG. 5). In the non-cooling position, a distal end of the cooling member 200 is displaced proximally from the energy probe 132 so as to impede thermal conduction between the energy probe 132 and the cooling member 200. In the cooling position, the distal end of the cooling member 200 thermally contacts the energy probe 132 so as to facilitate thermal conduction between the energy probe 132 and the cooling member 200.

For the purposes of the present disclosure and appended claims, "thermal contact" of two members can be achieved by direct contact between the members, or by a thermally conductive element separating and in contact with both members. Examples of such a thermally conductive element can include thermal tape, thermal paste or grease, solder, metal foil, and so on. In some instances it may be desirable to employ a thermally conductive element that is electrically insulating, e.g., a silicone-based thermal grease. For the purposes of the present disclosure and appended claims, "thermally insulating" shall designate a material having thermal conductivity less than $0.5$ W m$^{-1}$ K$^{-1}$, and "thermally conductive" shall designate a material having thermal conductivity greater than $0.5$ W m$^{-1}$ K$^{-1}$.

A method employing the surgical apparatus comprises: positioning the surgical instrument 10 so that the energy probe 132 is in contact with a target tissue; during a selected time interval, transmitting energy from the energy source 20 distally along the energy conductor 115 to the energy probe 132; and, at the end of the selected time interval, discontinuing energy transmission. The energy is transmitted with the cooling member 200 in the non-cooling position and the energy probe 132 in contact with the target tissue, so that the heat generated or deposited in the tissue cannot readily flow out of the tissue and proximally along the cooling member 200. Upon discontinuing the energy transmission (at the end of the time interval), the cooling member 200 is moved into the cooling position, so that residual heat can flow out of the tissue, through the energy probe 132, and proximally along the cooling member 200 to the cooler 210, where the heat is dissipated. By providing such controlled cooling of the heated tissue, undesirable effects of excessive energy deposition in the tissue can be reduced or avoided.

Figure 5:
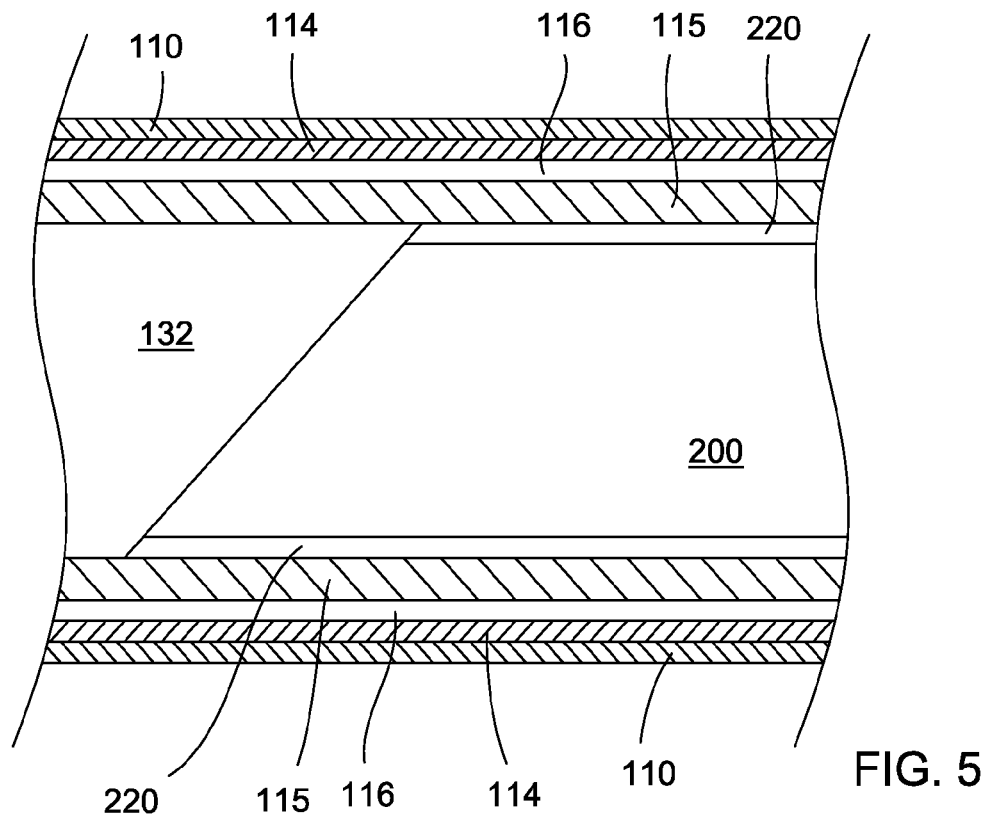
FIG. 5 is a longitudinal section of a portion of the surgical instrument with the cooling member in a distal, cooling position.

In some examples of the surgical apparatus 10, the energy conductor 115 comprises an elongated hollow tube and the cooling member 200 is a rod reciprocally movable within the energy conductor 115 (FIGS. 3-5). In other examples, the cooling member 200 comprises an elongated hollow tube, the energy conductor 115 is positioned within the cooling member 200, and the cooling member 200 is reciprocally movable relative to the energy conductor 115. Other suitable arrangements can be employed, e.g., wherein the cooling member 200 and the energy conductor 115 are arranged side-by-side within the sheath 110 (not necessarily in contact with each other).

In some examples a thermal insulator 220 can be arranged to impede thermal conduction between the cooling member 200 and the energy conductor 115 or between the cooling member 200 and the sheath 110. Thermal insulation of the cooling member 200 is desirable so that, with the cooling member 200 in the non-cooling position (i.e., proximally spaced apart from the energy probe 132), lateral contact of the cooling member 200 with the energy conductor 115 or the sheath 110 along their respective lengths does not provide an alternative, high conductance path for heat to flow proximally away from the energy probe 132 and the heated tissue. Without that alternative conduction path and with the cooling member 200 in the non-conducting position, premature proximal conduction by the cooling member 200 of heat generated or deposited in the target tissue is reduced or eliminated, enabling the target tissue to be heated more quickly or to a higher temperature. In other examples, the thermal insulator 220 may not be necessary; arranging the energy conductor 115 to have a much smaller cross-sectional area than the cooling member 200 can in some instances sufficiently impede heat flow from the energy probe 132 to the cooling member 200 with the cooling member in the non-cooling position. The thermal insulator 220 can comprise any one or more suitable thermally insulating materials, e.g., polymer, plastic, or other thermally insulating materials.

In examples wherein one of the energy conductor 115 or the cooling member 200 is an elongated tube and the other one is positioned within the tube, the thermal insulator 220 can be arranged as an elongated hollow cylindrical sleeve separating the energy conductor 115 from the cooling member 200 over much of their respective lengths, as an elongated sleeve separating the energy conductor 115 from the cooling member 200 over much of their respective lengths and having a series of annular inward or outward flanges spaced along its length, or as a series of discrete annular members spaced along the respective lengths of the energy conductor 115 and the cooling member 200. The first two arrangements can be more suitable in examples wherein the energy source 20 is an RF electrical energy source, to also provide electrical insulation between the cooling member 200 and the energy conductor 115; the latter two arrangements can be more suitable in examples wherein the energy source 20 is an ultrasonic energy source, to reduce coupling of ultrasonic energy from the energy conductor 115 into the cooling member 200. In any of those arrangements, the thermal insulator 220 can also act as a mechanical bearing that facilitates movement of the cooling member 200 relative to the energy conductor 115 between the cooling and non-cooling positions. In examples wherein the energy conductor 115 comprises an elongated hollow tube and the cooling member 200 is reciprocally movable within the energy conductor 115, the thermal insulator 220 between the cooling member 200 and the energy conductor 115 also acts to impede thermal conduction between the cooling member 200 and the sheath 110. In other examples (e.g., energy conductor 115 within tubular cooling member 200, or side-by-side energy conductor 115 and cooling member 200), an additional thermal insulator can be employed to impede thermal conduction between the cooling member 200 and the sheath 110.

To provide a sufficient differential of the overall thermal conductance of the surgical instrument 10 between the cooling and non-cooling positions of the cooling member 200, the longitudinal thermal conductance per unit length of the cooling member 200 preferably exceeds the combined longitudinal thermal conductance per unit length of the sheath 110 and the energy conductor 115. In that case, overall longitudinal thermal conductance per unit length of the surgical instrument 10 at least doubles with the cooling member 200 in the cooling position relative to the non-cooling position. Even larger thermal conductance differentials can be desirable to provide more rapid cooling of the heated tissue and energy probe 132. In various examples, the longitudinal thermal conductance per unit length of the cooling member 200 can exceed the combined longitudinal thermal conductance per unit length of the sheath 110 and the energy conductor 115 by a factor of at least 2×, 5×, 10×, 20×, 50×, or even more.

Note that longitudinal thermal conductance per unit length is an extensive property of the cooling member 200, the energy conductor 115, and the sheath 110 that depends on the cross sectional area of each member and the thermal conductivity of the respective materials employed. Thermal conductivity, on the other hand, is an intensive property of a material that does not depend on the amount of material or its arrangement. The thermal conductance differential discussed above can be achieved by employing a cooling member 200 having thermal conductivity greater than that of the sheath 110 or the energy conductor 115, a total cross-sectional area greater than the combined cross-sectional areas of the sheath 110 and the energy conductor 115, or both. Regardless of the relative cross-sectional areas, typically materials are employed so that thermal conductivity of the cooling member 200 exceeds thermal conductivity of the sheath 110 and exceeds thermal conductivity of the energy conductor 115. In various examples, thermal conductivity of the cooling member 200 can exceed thermal conductivity of the sheath 110 by a factor of at least 2×, 5×, 10×, 20×, or even more; in various examples, thermal conductivity of the cooling member 200 can exceed thermal conductivity of the energy conductor 115 by a factor of at least 2×, 5×, 10×, 20×, or even more. Examples of suitable materials for the cooling member 200 can include, but are not limited to, silver, gold, copper, copper alloys (e.g., brass), or aluminum, which each have thermal conductivity greater than 100 W m$^{-1}$K$^{-1}$. In many examples of the surgical instrument 10, the sheath 110 or the energy conductor 115 can comprise titanium or stainless steel, which have thermal conductivities in the range of 5-30 W m$^{-1}$ K$^{-1}$; the preceding examples of materials for the cooling member 200 would be suitable for use in such examples of the surgical instrument 10. Other suitable combinations of one or more sheath materials, one or more energy conductor materials, and one or more cooler rod materials can be employed. Material suitability can be based on any set of necessary or desirable criteria or properties, including mechanical properties (e.g., strength, stiffness, density), chemical properties (e.g., solubility, corrosion resistance, biocompatibility, electrochemical potential), thermal properties (e.g., heat capacity, thermal conductivity, and so on), electrical properties (e.g., electrical conductivity or resistivity), acoustic properties (e.g., transmission of ultrasonic energy) or other material properties. Metals, alloys, plastics, and polymers are often employed.

In some examples the energy probe 132 can comprise the same material as the energy conductor 115. In other examples, to further enhance cooling of heated tissue by proximal thermal conduction along the cooling member 200, the energy probe can comprise one or more materials having thermal conductivity higher than that of the energy conductor 115. In some of those instances, if the cooling member material has suitable other properties (mechanical, electrical, and so on) the energy probe 132 can comprise the same material. In some other instances, if the cooling member material is not suitable for use as the energy probe 132, a material with suitable properties can be employed that differs from both the cooling member 200 and the energy conductor 115 and that has higher thermal conductivity than the energy conductor 115. In one such specific instance, the energy conductor 115 can comprise titanium or stainless steel, the cooling member 200 can comprise silver, and the energy probe 132 can comprise tungsten, copper, copper alloy (e.g., brass), or aluminum.

Any suitable type of cooler 210 can be employed. One example of a suitable cooler 210 is a thermoelectric cooler. The cooler 210 is thermally coupled to a proximal portion of the cooling member 200 and typically is operated substantially continuously during use of the surgical instruments 10 to keep the cooling member 200 at a substantially constant temperature while in the non-cooling position. Upon movement of the cooling member 200 into the cooling position, thermal conduction from the energy probe 132 into the cooling member 200 results in a longitudinal temperature gradient along the cooling member 200 and proximal heat flow through the cooling member 200 to the cooler 210, where the heat is dissipated. The surgical instrument 10 can include the cooler 210, or the cooler 210 can be provided as a separate component.

The cooling capability employing the cooling member 200 described above can be employed in any energized surgical instrument 10 that operates by heating targeted tissues in a patient's body. Common examples of such energized surgical instruments include examples in which: (i) the energy source 20 is an ultrasonic source, the energy conductor 115 conducts ultrasonic energy, and the energy probe 132 is an ultrasonic probe; (ii) the energy source 20 is an RF electrical source, the energy conductor 115 conducts RF electrical energy, and the energy probe 132 is a single monopolar electrode or a first electrode of a pair of bipolar electrodes; or the energy source 20 provides both ultrasonic and RF electrical energy (from a single unit or from separate units), the energy conductor 115 conducts both ultrasonic and RF electrical energy, and the energy probe 132 is both an ultrasonic probe and an electrode (monopolar or bipolar). Whatever type of energy source is employed, the surgical instrument 10 can include the energy source 20 (ultrasonic, RF electrical, both, or other; single or multiple units), or the energy source 20 can be provided as one or more separate components. The energy source 20 is coupled to a proximal portion of the energy conductor 115, which is in turn arranged to transmit distally to the energy probe 132 the energy (whatever its type) supplied by the energy source 20.

Various examples of the surgical instrument 10 can include a cooling control member 124 coupled to the cooling member 200 so that manipulation of the cooling control member 124 causes movement of the cooling member 200 between the cooling position and the non-cooling position. The cooling control member 124 can be provided in any suitable arrangement or form factor, e.g., a button, a lever, a trigger, a knob, a switch, and so forth. Various examples of the surgical instrument 10 can include an energy control member of any suitable type coupled to the energy source 20 or the energy conductor 115 to control transmission of energy to the energy probe 132. In some of those latter examples, the cooling control member 124 can also serve as the energy control member so that: (i) manipulation of the control member 124 to cause energy transmission from the energy source 20 along the energy conductor 115 to the energy probe 132 also causes movement of the cooling member 200 from the cooling position to the non-cooling position; and (ii) manipulation of the control member 124 to discontinue energy transmission from the energy source 20 along the energy conductor 115 to the energy probe 132 also causes movement of the cooling member 200 from the non-cooling position to the cooling position. In examples in which multiple types of energy can be transmitted from the energy source 20 distally along the energy conductor 115 to the energy probe 132, multiple energy control members of any suitable type can be employed to control transmission of the corresponding types of energy (with or without concomitant movement of the cooling member 200), or a single control member of any suitable type can be employed to selectively activate one or more types of energy transmission (with or without concomitant movement of the cooling member 200). Any control member employed can be positioned on the handle 120 if present.

In some examples of the surgical instrument 10, the energy probe 132 is arranged to act as a first jaw of a pair of jaws. A second jaw 134 of the pair of jaws can be pivotably connected to the sheath 110 or to the energy conductor 115 so that the pair of jaws is movable between an open arrangement and a closed arrangement. In the open position, the jaws can be positioned around one or more portions of tissue to be cut, sealed, or coagulated. In the closed position, the jaws can hold or grasp one or more portions of tissue while they are cut, sealed, or coagulated. Some of those examples can include a jaw control member of any suitable type coupled to the pair of jaws so that manipulation of the jaw control member causes movement of the pair of jaws between the open and closed arrangements; in such embodiments the surgical apparatus 10 also typically includes an elongated jaw actuator 114 within the sheath 110 coupling the jaw control member to the second jaw 134. The jaw control member can be provided as a separate control member, an energy control member can also serve as the jaw control member, or the cooling control member 124 can also serve as the jaw control member (with or without also serving as an energy control member); the jaw control member can be positioned on handle portion 120 if present. It is typically the case that the pair of jaws (i) would be in the closed position while energy is transmitted to the energy probe 132 and the cooling member 200 is in the non-cooling position, and (ii) would be in the open position while the cooling member is in the cooling position and energy is not transmitted to the energy probe 132.

In some examples of the surgical apparatus 10 having a pair of jaws, the energy probe 132 acts as a first electrode of a pair of bipolar electrodes and the second jaw 134 acts as a second electrode of the pair of bipolar electrodes. In such examples, the energy source provides RF electrical energy to the energy probe 132 through the energy conductor 115, while the second jaw 134 is separately connected to the energy source 20. That separate connection can be made through the jaw actuator 114. In those examples, an electrical insulator 116 typically is employed to isolate the energy conductor 115 from the jaw actuator 114. Any one or more suitable electrical insulating materials can be employed, e.g., plastic, polymer, or other electrical insulating material. The electrical insulator can also serve as a mechanical bearing for facilitating longitudinal movement of the jaw actuator 114 within the sheath 110.

It may be desirable in examples having a pair of jaws to arrange the cooling member 200 so that: (i) in the cooling position, the cooling member 200 thermally contacts the second jaw 134 or the jaw actuator 114 so as to facilitate thermal conduction between the second jaw 134 and the cooling member 200; and (ii) in the non-cooling position, the cooling member 200 is separated from the second jaw 134 and the actuator 114 so as to impede thermal conduction between the second jaw 134 and the cooling member 200. In some examples, thermal contact between the cooling member 200 and the second jaw 134 or the actuator 114 is provided by direct contact between the cooling member 200 and the second jaw 134 or the actuator 114. In other examples, thermal contact between the second jaw 134 or the actuator 114 is provided by a thermally conductive element separating and in contact with the cooling member 200 and the second jaw 134 or the actuator 114, e.g., thermal tape, thermal paste or grease, solder, metal foil, and so on. However, in examples in which cooling of the second jaw 134 is desired and the second jaw 134 acts as a bipolar electrode, the thermally conductive element should also be electrically insulating, e.g., a silicone-based thermal grease. The second jaw 134 can comprise any one or more suitable materials, including but not limited to those materials employed in the sheath 110, energy conductor 115, or energy probe 132, based on any one or more necessary or desirable material properties.

In addition to the preceding, the following examples fall within the scope of the present disclosure or appended claims:

Example 1

A surgical apparatus comprising: an elongated sheath including a distal end portion and a proximal end portion; an energy probe connected to the distal end portion of the sheath; an elongated energy conductor contained within the sheath and arranged to transmit distally to the energy probe energy from an energy source; and an elongated cooling member reciprocally movable within the sheath and thermally coupled at a proximal portion of the cooling member to a cooler, wherein: the cooling member is movable between a proximal, non-cooling position and a distal, cooling position; in the non-cooling position, a distal end of the cooling member is displaced proximally from the energy probe so as to impede thermal conduction between the energy probe and the cooling member; and in the cooling position, the distal end of the cooling member thermally contacts the energy probe so as to facilitate thermal conduction between the energy probe and the cooling member.

Example 2

The surgical apparatus of Example 1 wherein thermal contact between the energy probe and the cooling member is established by direct contact between the energy probe and the cooling member.

Example 3

The surgical apparatus of Example 1 wherein thermal contact between the energy probe and the cooling member is established by a thermally conductive element separating and in contact with the energy probe and the cooling member.

Example 4

The surgical apparatus of any one of Examples 1 through 3 further comprising a thermal insulator arranged to impede lateral thermal conduction between the cooling member and the energy conductor and between the cooling member and the sheath.

Example 5

The surgical apparatus of Example 4 wherein the thermal insulator comprises plastic or polymer.

Example 6

The surgical apparatus of any one of Examples 1 through 5 wherein the energy conductor comprises an elongated hollow tube and the cooling member is an elongated rod reciprocally movable within the energy conductor.

Example 7

The surgical apparatus of any one of Examples 1 through 5 wherein the cooling member comprises an elongated hollow tube and the energy conductor is an elongated rod within the cooling member and the cooling member is reciprocally movable relative to the energy conductor.

Example 8

The surgical apparatus of any one of Examples 1 through 5 wherein the energy conductor and the cooling member are arranged side-by-side within the sheath.

Example 9

The surgical apparatus of any one of Examples 1 through 8 wherein longitudinal thermal conductance per unit length of the cooling member exceeds combined longitudinal thermal conductance per unit length of the sheath and the energy conductor.

Example 10

The surgical apparatus of any one of Examples 1 through 9 wherein longitudinal thermal conductance per unit length of the cooling member is greater than about 2×, 5×, 10×, 20×, or 50× combined longitudinal thermal conductance per unit length of the sheath and the energy conductor.

Example 11

The surgical apparatus of any one of Examples 1 through 10 wherein thermal conductivity of the cooling member exceeds thermal conductivity of the sheath and exceeds thermal conductivity of the energy conductor.

Example 12

The surgical apparatus of any one of Examples 1 through 11 wherein thermal conductivity of the cooling member is greater than about 2×, 5×, 10×, or 20× the thermal conductivity of the sheath and is greater than about 2×, 5×, 10×, or 20× the thermal conductivity of the energy conductor.

Example 13

The surgical apparatus of any one of Examples 1 through 12 wherein the cooling member comprises silver, gold, copper, copper alloy, or aluminum.

Example 14

The surgical apparatus of any one of Examples 1 through 13 wherein the energy conductor comprises titanium or stainless steel or the sheath comprises titanium or stainless steel.

Example 15

The surgical apparatus of any one of Examples 1 through 14 wherein the cooler comprises a thermoelectric cooler.

Example 16

The surgical apparatus of any one of Examples 1 through 15 further comprising the cooler thermally coupled to a proximal portion of the cooling member.

Example 17

The surgical apparatus of any one of Examples 1 through 16 wherein the energy conductor is arranged to transmit distally to the energy probe ultrasonic energy from an ultrasonic energy source.

Example 18

The surgical apparatus of Example 17 further comprising the ultrasonic energy source coupled to a proximal portion of the energy conductor.

Example 19

The surgical apparatus of any one of Examples 1 through 18 wherein the energy conductor is arranged to transmit distally to the energy probe RF electrical energy from an RF electrical energy source.

Example 20

The surgical apparatus of Example 19 further comprising the RF electrical energy source coupled to a proximal portion of the energy conductor.

Example 21

The surgical apparatus of any one of Examples 19 or 20 wherein the energy probe is connected to the energy conductor as a first electrode of a pair of bipolar electrodes.

Example 22

The surgical apparatus of Example 21 wherein: the energy probe is arranged as a first jaw of a pair of jaws; the distal portion includes a second jaw of the pair of jaws, the second jaw being pivotably connected to the sheath or the distal end portion so that the pair of jaws is movable between an open arrangement and a closed arrangement; and the second jaw is connected to the RF electrical energy source as a second electrode of the pair of bipolar electrodes.

Example 23

The surgical apparatus of any one of Examples 19 or 20 wherein the energy probe is connected to the energy conductor as a single monopolar electrode.

Example 24

The surgical apparatus of any one of Examples 1 through 23 further comprising a handle portion connected to the proximal end portion of the sheath.

Example 25

The surgical apparatus of any one of Examples 1 through 24 further comprising a cooling control member coupled to the cooling member so that manipulation of the cooling control member causes movement of the cooling member from the cooling position to the non-cooling position or from the non-cooling position to the cooling position.

Example 26

The surgical apparatus of any one of Examples 1 through 24 further comprising an energy control member coupled to the cooling member and to the energy source or the energy conductor so that: (i) manipulation of the energy control member to cause energy transmission from the energy source along the energy conductor to the energy probe also causes movement of the cooling member from the cooling position to the non-cooling position; and (ii) manipulation of the energy control member to discontinue energy transmission from the energy source along the energy conductor to the energy probe also causes movement of the cooling member from the non-cooling position to the cooling position.

Example 27

The surgical apparatus of any one of Examples 1 through 26 wherein: the energy probe is arranged to act as a first jaw of a pair of jaws; and the distal portion includes a second jaw of the pair of jaws, the second jaw being pivotably connected to the sheath or the distal end portion so that the pair of jaws is movable between an open arrangement and a closed arrangement.

Example 28

The surgical apparatus of Example 27 further comprising a jaw control member coupled to the pair of jaws so that manipulation of the jaw control member causes movement of the pair of jaws between the open and closed arrangements.

Example 29

The surgical apparatus of any one of Examples 22, 27, or 28 wherein: in the non-cooling position, the cooling member is separated from the second jaw or an actuator of the second jaw so as to impede thermal conduction between the second jaw and the cooling member; and in the cooling position, the cooling member thermally contacts the second jaw or the actuator so as to facilitate thermal conduction between the second jaw and the cooling member.

Example 30

The surgical apparatus of Example 29 wherein thermal contact between the cooling member and the second jaw or the actuator is provided by direct contact between the cooling member and the second jaw or the actuator.

Example 31

The surgical apparatus of Example 29 wherein thermal contact between the second jaw or the actuator is provided by a thermally conductive element separating and in contact with the cooling member and the second jaw or the actuator.

Example 32

The surgical apparatus of any one of Examples 22 or 27 through 31 wherein thermal conductivity of the second jaw exceeds thermal conductivity of the sheath and exceeds thermal conductivity of the energy conductor.

Example 33

The surgical apparatus of any one of Examples 22 or 27 through 32 wherein the second jaw comprises tungsten, copper, copper alloy, or aluminum.

Example 34

A method employing the surgical apparatus of any one of Examples 1 through 33, the method comprising: positioning the surgical instrument so that the energy probe is in contact with a target tissue; with the cooling member in the non-cooling position and the energy probe in contact with the target tissue, transmitting energy from the energy source distally along the energy conductor to the energy probe during a selected time interval; discontinuing energy transmission along the energy conductor at the end of the selected time interval; and after the selected time interval, moving the cooling member into the cooling position.

It is intended that equivalents of the disclosed example embodiments and methods shall fall within the scope of the present disclosure or appended claims. It is intended that the disclosed example embodiments and methods, and equivalents thereof, may be modified while remaining within the scope of the present disclosure or appended claims.

In the foregoing Detailed Description, various features may be grouped together in several example embodiments for the purpose of streamlining the disclosure. This method of disclosure is not to be interpreted as reflecting an intention that any claimed embodiment requires more features than are expressly recited in the corresponding claim. Rather, as the appended claims reflect, inventive subject matter may lie in less than all features of a single disclosed example embodiment. Thus, the appended claims are hereby incorporated into the Detailed Description, with each claim standing on its own as a separate disclosed embodiment. However, the present disclosure shall also be construed as implicitly disclosing any embodiment having any suitable set of one or more disclosed or claimed features (i.e., a set of features that are neither incompatible nor mutually exclusive) that appear in the present disclosure or the appended claims, including those sets that may not be explicitly disclosed herein. It should be further noted that the scope of the appended claims does not necessarily encompass the whole of the subject matter disclosed herein.

For purposes of the present disclosure and appended claims, the conjunction "or" is to be construed inclusively (e.g., "a dog or a cat" would be interpreted as "a dog, or a cat, or both"; e.g., "a dog, a cat, or a mouse" would be interpreted as "a dog, or a cat, or a mouse, or any two, or all three"), unless: (i) it is explicitly stated otherwise, e.g., by use of "either . . . or," "only one of," or similar language; or (ii) two or more of the listed alternatives are mutually exclusive within the particular context, in which case "or" would encompass only those combinations involving non-mutually-exclusive alternatives. For purposes of the present disclosure and appended claims, the words "comprising," "including," "having," and variants thereof, wherever they appear, shall be construed as open ended terminology, with the same meaning as if the phrase "at least" were appended after each instance thereof.

In the appended claims, if the provisions of 35 USC §112 ¶6 are desired to be invoked in an apparatus claim, then the word "means" will appear in that apparatus claim. If those provisions are desired to be invoked in a method claim, the words "a step for" will appear in that method claim. Conversely, if the words "means" or "a step for" do not appear in a claim, then the provisions of 35 USC §112 ¶6 are not intended to be invoked for that claim.

If any one or more disclosures are incorporated herein by reference and such incorporated disclosures conflict in part or whole with, or differ in scope from, the present disclosure, then to the extent of conflict, broader disclosure, or broader definition of terms, the present disclosure controls. If such incorporated disclosures conflict in part or whole with one another, then to the extent of conflict, the later-dated disclosure controls.

The Abstract is provided as required as an aid to those searching for specific subject matter within the patent literature. However, the Abstract is not intended to imply that any elements, features, or limitations recited therein are necessarily encompassed by any particular claim. The scope of subject matter encompassed by each claim shall be determined by the recitation of only that claim.

What is claimed is:

1. A surgical apparatus comprising:
   (a) an elongated sheath including a distal end portion and a proximal end portion;
   (b) an energy probe connected to the distal end portion of the sheath;
   (c) an elongated energy conductor contained within the sheath and arranged to transmit distally to the energy probe energy from an energy source; and
   (d) an elongated cooling member reciprocally movable within the sheath and thermally coupled at a proximal portion of the cooling member to a cooler,
   wherein:
   (e) the cooling member is movable between a proximal, non-cooling position and a distal, cooling position;
   (f) in the non-cooling position, a distal end of the cooling member is displaced proximally from the energy probe so as to impede thermal conduction between the energy probe and the cooling member; and
   (g) in the cooling position, the distal end of the cooling member thermally contacts the energy probe so as to facilitate thermal conduction between the energy probe and the cooling member,
   (h) wherein the energy conductor comprises an elongated hollow tube and the cooling member is an elongated rod reciprocally movable within the energy conductor.

2. The surgical apparatus of claim 1 further comprising a thermal insulator arranged to impede lateral thermal conduction between the cooling member and the energy conductor and between the cooling member and the sheath.

3. The surgical apparatus of claim 1 wherein longitudinal thermal conductance per unit length of the cooling member exceeds combined longitudinal thermal conductance per unit length of the sheath and the energy conductor.

4. The surgical apparatus of claim 1 wherein thermal conductivity of the cooling member exceeds thermal conductivity of the sheath and exceeds thermal conductivity of the energy conductor.

5. The surgical apparatus of claim 4 wherein the cooling member comprises silver, gold, copper, copper alloy, or aluminum.

6. The surgical apparatus of claim 4 wherein the energy conductor comprises titanium or stainless steel or the sheath comprises titanium or stainless steel.

7. The surgical apparatus of claim 1 wherein the cooler comprises a thermoelectric cooler.

8. The surgical apparatus of claim 1 wherein the energy conductor is arranged to transmit distally to the energy probe ultrasonic energy from an ultrasonic energy source.

9. The surgical apparatus of claim 1 wherein the energy conductor is arranged to transmit distally to the energy probe RF electrical energy from an RF electrical energy source.

10. The surgical apparatus of claim 9 wherein the energy probe is connected to the energy conductor as a first electrode of a pair of bipolar electrodes.

11. The surgical apparatus of claim 9 wherein the energy probe is connected to the energy conductor as a single monopolar electrode.

12. The surgical apparatus of claim 1 further comprising a cooling control member coupled to the cooling member so that manipulation of the cooling control member causes movement of the cooling member from the cooling position to the non-cooling position or from the non-cooling position to the cooling position.

13. The surgical apparatus of claim 1 further comprising an energy control member coupled to the cooling member and to the energy source or the energy conductor so that: (i) manipulation of the energy control member to cause energy transmission from the energy source along the energy conductor to the energy probe also causes movement of the cooling member from the cooling position to the non-cooling position; and (ii) manipulation of the energy control member to discontinue energy transmission from the energy source along the energy conductor to the energy probe also causes movement of the cooling member from the non-cooling position to the cooling position.

14. The surgical apparatus of claim 1 wherein:
   (i) the energy probe is arranged to act as a first jaw of a pair of jaws; and
   (ii) a second jaw of the pair of jaws is pivotably connected to the sheath or the energy conductor so that the pair of jaws is movable between an open arrangement and a closed arrangement.

15. A method employing the surgical apparatus of claim 1, the method comprising:
   (i) positioning the surgical instrument so that the energy probe is in contact with a target tissue;
   (ii) with the cooling member in the non-cooling position and the energy probe in contact with the target tissue, transmitting energy from the energy source distally along the energy conductor to the energy probe during a selected time interval; and
   (iii) discontinuing energy transmission along the energy conductor at the end of the selected time interval; and
   (iv) after the selected time interval, moving the cooling member into the cooling position.

* * * * *